United States Patent [19]

Cram et al.

[11] Patent Number: 4,859,606
[45] Date of Patent: Aug. 22, 1989

[54] METHOD FOR DETECTING CATIONS IN A TEST SAMPLE UTILIZING CHROMOGENIC CRYPTAHEMISPHERANDS

[75] Inventors: Donald J. Cram, Los Angeles, Calif.; Eddy Chapoteau, Brooklyn, N.Y.; Bronislaw P. Czech, Peekskill, N.Y.; Carl R. Gebauer, Crompond, N.Y.; Roger C. Helgeson, Canuga Park, Calif.; Anand Kumar, Southfields; Koon-Wah Leong, Ossining, both of N.Y.

[73] Assignees: Technicon Instruments Corporation, Tarrytown, N.Y.; The Regents of the University of California, Berkeley, Calif.

[21] Appl. No.: 38,681

[22] Filed: Apr. 15, 1987

[51] Int. Cl.[4] .................. C07D 498/18; C07D 513/18; C07D 273/00; C07C 107/04
[52] U.S. Cl. ........................ 436/79; 422/50; 422/68; 534/752; 540/469
[58] Field of Search ................ 534/752; 540/469; 436/79; 422/50, 68

[56] References Cited

U.S. PATENT DOCUMENTS

| | | | |
|---|---|---|---|
| 3,847,949 | 11/1974 | Pedersen et al. | 540/469 |
| 3,966,766 | 6/1976 | Lehn | 540/469 X |
| 4,076,724 | 2/1978 | Lehn | 540/469 |
| 4,080,337 | 3/1978 | Cram | 540/469 |

FOREIGN PATENT DOCUMENTS

| | | | |
|---|---|---|---|
| 2853064 | 6/1980 | Fed. Rep. of Germany | 540/469 |
| 3202779 | 8/1983 | Fed. Rep. of Germany | 534/752 |
| 1139730 | 2/1985 | U.S.S.R. | 534/469 |

*Primary Examiner*—Floyd D. Higel
*Attorney, Agent, or Firm*—Jeffrey M. Greenman

[57] ABSTRACT

The present invention resides in the discovery of a class of compounds defined herein as "chromogenic cryptahemispherands" useful for the measurement of ions, in particular, ions in aqueous solution, which have the structure

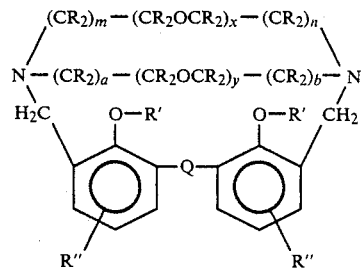

wherein:
R, same or different, is hydrogen, lower alkyl, lower alkylidene, lower alkenyl, allyl or aryl;
R', same or different, is lower alkyl, lower alkylidene, lower alkenyl, allyl or aryl;
R'', same or different, is hydrogen, lower alkyl, lower alkylidene, lower alkenyl, allyl or aryl;
Q is a chromogenic moiety capable of providing the appearance of or change in color, or which is otherwise capable of providing a detectable response in the presence of a particular cation;
a, b, m and n, same or different, are 1 to about 3; and x, y, same or different, are 1 to about 4.

A test device utilizing one or more of the compounds for performing such measurements is also disclosed.

6 Claims, 7 Drawing Sheets

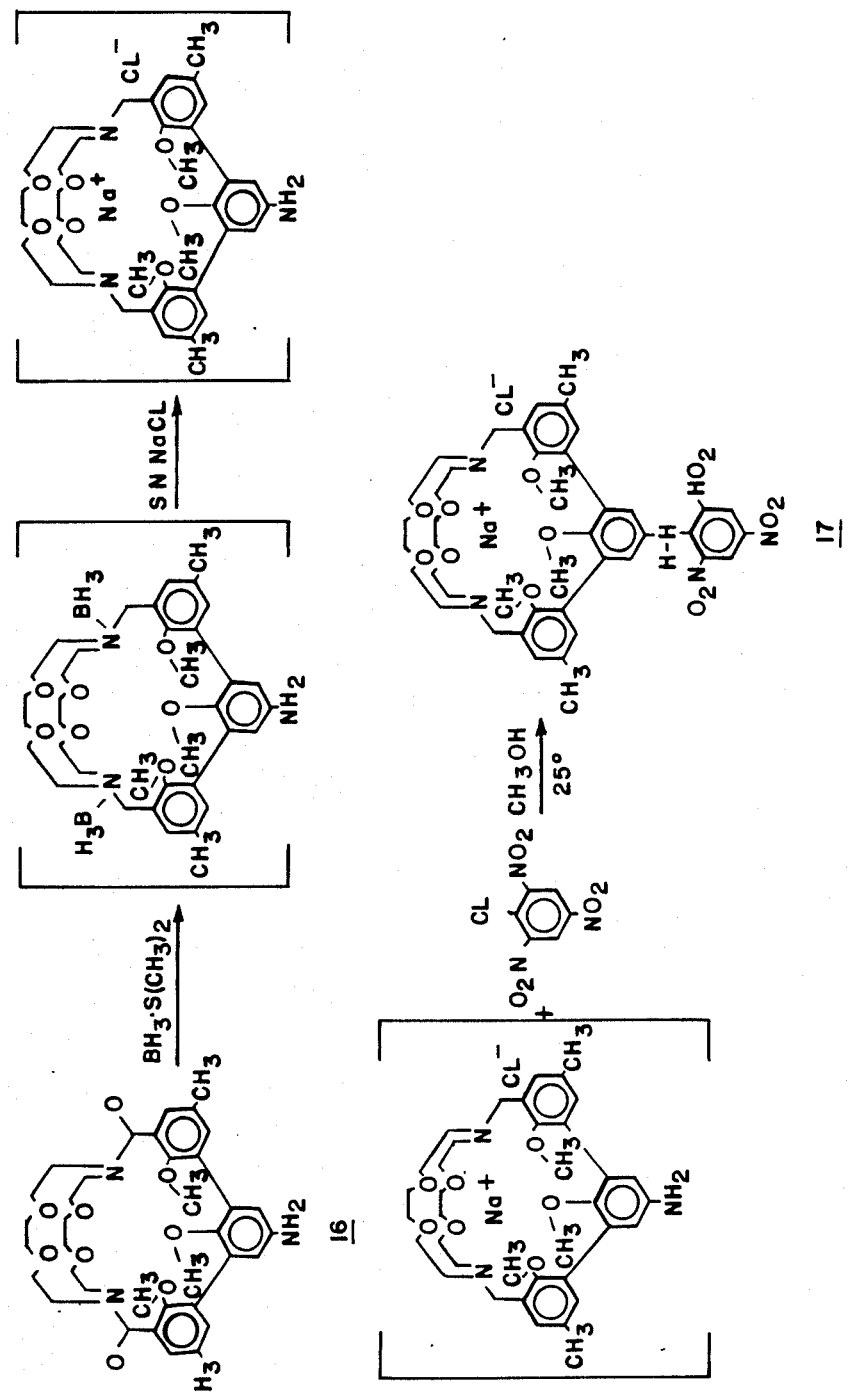
FIG.IC

METHOD FOR DETECTING CATIONS IN A TEST SAMPLE UTILIZING CHROMOGENIC CRYPTAHEMISPHERANDS

CONTENTS

Section

1. Introduction
2. Background of the Invention
   2.1 Ion-selective Electrodes
   2.2 Liquid/Liquid Partitioning
   2.3 Fluorescent Anions
   2.4 Reporter Substances
   2.5 Ionophores
      2.5.1 Podands
      2.5.2 Corands
      2.5.3 Cryptands
      2. 5.4 Hemispherands
      2.5.5 Spherands
      2.5.6 Cryptahemispherands
   2.6 Chromogenic Ionophores
   2.7 Synopsis
3. Brief Description of the Drawings
4. Summary of the Invention
Definitions
   5.1 "Ionophore"
   5.2 "Chromogenic"
   5.3 "Detectable Response"
   5.4 "Lower Alkyl, Lower Alkylidene, Lower Alkenyl"
   5.5 "Aryl"
   5.6 "Electron Withdrawing Group"
6. The Chromogenic Cryptahemispherand
   6.1 Cationic Adaptability
   6.2 The Chromogenic Moiety
   6.3 Presently Preferred Embodiment
7. The Test Composition Section 8. The Test Device
   8.1 The Carrier Matrix
   8.2 Making the Test Device
9. Use of the Invention
10. Experimental
    10. 1 Synthesis of a Preferred Chromogenic Cryptahemispherand
    10. 2 A Preferred Aqueous System for Potassium Determination
    10. 3 Use of a Preferred Aqueous System for Serum Determination of Potassium
    10.4 Effect of pH on Potassium/Sodium Selectivity in a Liquid/Liquid Partitioning System
    10. 5 Effect of pH and a Water-Miscible Organic Solvent on Potassium/Sodium Selectivity in an Aqueous System
    10. 6 A Model Test Device
    10. 7 Test Device for Detecting Potassium in Serum
    10. 8 A Preferred Aqueous System for Sodium (Rate) Measurement
    10.9 A Preferred Aqueous System for Sodium (End Point) Measurement
    10.10 Test Device for Detecting Sodium Ions
11. What is Claimed
12. Abstract of the Disclosure

1. INTRODUCTION

The present invention relates to a novel class of compounds useful for the measurement of ions, in particular ions in aqueous solution, and to a test means or device utilizing one or more of the compounds for performing such measurements. The invention provides a quick, facile way of assaying such ions whereby results are available to the assayist momentarily after merely contacting a test sample solution with the test means or device. There is no need for cumbersome, expensive electronic equipment such as ion-selective electrodes, flame photometers, atomic absorption spectrophotometers or the like. Nor is it necessary to resort to time-consuming wet chemistry techniques such as titration and other laboratory procedures The present invention enables the analyst to merely contact the test sample with a test composition or a dry test device, test slide, or similar test means or configuration, and observe any color change or other detectable response. Finally, the present invention enables an unusually fast assay and unexpectedly high degree of selectivity, thereby permitting the detection of relatively low concentrations of an analyte ion even in solutions having relatively high concentrations of different, potentially interfering ions, while providing selectivity and accuracy to a degree heretofore unknown.

The determination of aqueous ion concentration has application in numerous technologies. In the water purification art, calcium concentration must be carefully monitored to assess the degree of saturation of an ion exchange resin deionizer. Measurement of sodium and other ions in seawater is important in the preparation of drinking water aboard a ship at sea. Measurement of the potassium level in blood aids the physician in the diagnosis of conditions leading to muscle irritability and excitatory changes in myocardial function. Such conditions include oliguria, anuria, urinary obstruction and renal failure due to shock.

Needless to say, a rapid, easy-to-perform method for determining the presence and concentration of a specific ion in aqueous samples would greatly enhance the state of these technologies, as well as any others where such quick, accurate determinations would be beneficial. Thus, for example, if a medical laboratory technician could accurately measure the potassium or sodium level of a serum, whole blood, plasma or urine sample in a matter of seconds or minutes, it would aid the physician in early diagnosis, and laboratory efficiency would increase manyfold. The present invention affords these and other unexpected advantages.

2. BACKGROUND OF THE INVENTION

Prior to the present invention, methods for determining ions in solution included flame photometry, atomic absorption photometry, ion-selective electrodes, multiple liquid phase partitioning and colorimetric slides. The use of certain compounds and compositions which selectively complex with, and therefore isolate, certain ions from the sample solution has become popular in ion-selective electrodes. These substances, known as ionophores, have the capability of selectively isolating ions from their counterions and other ions in a test sample, thereby causing a charge separation and a corresponding change in electrical conductivity in the phase containing the ionophore. Illustrative of other uses of the ion/ionophore phenomenon include ion assays utilizing membrane electrodes, liquid/liquid partitioning, fluorescence, various reporter substances, and chromogenic derivatives of certain ionophoric compounds.

2.1 Ion-Selective Electrodes (ISE)

When two solutions having different concentrations of ions are separated by an electrically conductive membrane, an electromotive force (EMF) can be generated. The EMF developed by such a system is a function of concentration or ionic activity of the solutions on either side of the membrane. This phenomenon is expressed mathematically by the well-known Nernst Equation $$E = \frac{RT}{nF} \ln \frac{\gamma_1 c_1}{\gamma_2 c_2} \quad (1)$$

in which E is the EMF of the particular system, F is the Faraday Constant, R is the gas constant, T is the temperature in °K and $\gamma$ and c are, respectively, the activity coefficients and molal concentrations of the ion under study. The subscript 1 designates the solution on one side of the membrane; the subscript 2 denotes the solution on the other side. The charge of the ion involved in the reaction is denoted by n.

In such membrane separation cells, the membrane can be a simple fritted glass barrier, allowing a small but measurable degree of ion diffusion from one solution to the other. Alternatively, a nonporous, electrically non-conductive film, such as polyvinyl chloride, impregnated with an ionophore can be employed. In the absence of the ionophore the film is an insulator and no EMF can be measured; when blended with an ionophore, charged ions are bound to the film and a small, measurable current can be induced to flow. Because the ionophore is selective in its affinity, and thus will bind only certain specific ions, such cells are ion selective. Any measurable EMF is due solely to the presence of those ions.

It is known that certain antibiotics, such as valinomycin, have an effect on the electrical properties of phospholipid bilayer membranes (biological membranes), such that these antibiotics effect solubilization of cations within the membrane, in the form of mobile charged complexes, thereby providing a "carrier" mechanism by which cations can cross the insulating hydrophobic or hydrocarbon interior of the membrane. Such complexes have the sole purpose of carrying the charge of the complex through the membrane. In an ISE they cause a voltage differential which can be determined between solutions on either side of the ISE membrane.

Thus, a cell for determining potassium ion can be produced through use of an ionophore specific for potassium (K+), e.g. valinomycin. In the presence of K+, valinomycin produces a concentration gradient across a membrane by binding and transporting the ion, thus generating a potential across the membrane. A reference concentration of K+ is placed on one side of the membrane and the test sample on the other. The EMF developed is measured using external reference electrodes and used to calculate the unknown concentration from equation (1). Because only K+ binds to the valinomycin in the membrane, the conductive path only appears for K+. Therefore, the EMF developed is attributable solely to the K+ concentration gradient across the membrane.

The current flowing across the membrane is so small that no significant quantity of K+ or counterion is transported through it. Electrical neutrality of the membrane is maintained either by a reverse flow of hydrogen ions (protons), or by a parallel flow of OH—.

A major difficulty in the use of such ion-selective electrodes has been the marked reduction of accuracy, selectivity and speed of response over time. Further, small changes in ion concentration produce such small changes in EMF that sophisticated voltmeter equipment is required.

Swiss patent application Ser. No. 11428/66, filed Aug. 9, 1966, describes the use of porous membranes impregnated with macrocyclic derivatives of amino and oxy-acids in ion-sensitive electrodes. Materials used to form the membrane are glass frits and other porous membranes. Such electrodes are said to be effective in measuring ion activities.

U.S. Pat. No. 4,053,381, issued to Hamblen, et al., discloses similar technology, and utilizes an ion specific membrane having ion mobility across it.

Liquid/Liquid Partitioning

Another known application of ionophores in ion determination is through liquid/liquid partitioning. Eisenman et al., *J. Membrane Biol.*, 1, 294–45 (1969), disclose the selective extraction of cations from aqueous solutions into organic solvents via macrotetralide actin antibiotics. In this procedure, a hydrophobic ionophore is dissolved in an organic solvent immiscible with water. The technique involves shaking an organic solvent phase containing the antibiotics with aqueous solutions containing cationic salts of lipid-soluble colored anions, such as picrates and dinitrophenolates. The intensity of color of the organic phase is then measured spectrophotometrically to indicate how much salt has been extracted. Phase transfer has also been studied by Dix et al., *Angew. Chem. Int. Ed. Engl.*, 17, 857 (1978) and is reported in reviews including Burgermeister et al., *Top. Curr. Chem.*, 69, 91 (1977); Yu et al., "Membrane Active Complexones," Elsevier, Amsterdam (1974); and Duncan, "Calcium in Biological Systems," Cambridge University Press (1976).

Sumiyoshi, et al., *Talanta*, 24, 763–765 (1977) describe another method useful for determining K+ in serum. In this technique serum is deproteinated by trichloroacetic acid, an indicator dye is added, and the mixture shaken with a solvent such as chloroform containing valinomycin.

Partitioning of a compound is rapid and effective between liquids, as shown by Eisenman, because of the mobility of the ionophore carrier and ions in their respective phases, which allows the transported species to diffuse rapidly away from the interface. Such a mechanism is normally impossible in the solid phase, because of the rigidity, immobility and essentially zero diffusion of materials in a solid phase.

2.3 Fluorescent Anions

Yet another approach to the measurement of ion activity in aqueous solutions utilizes fluorescent anions. Feinstein, et al., *Proc. Nat. Acad. Sci. U.S.A.*, 68, 2037–2041 (1971). It is stated that the presence of cation/ionophore complexes in organic solvents is known, but that complex formation in purely aqueous media had theretofore not been detected. Feinstein, et al., demonstrated the existence of such complexes in water through the use of the fluorescent salts 1-anilino-8-naphthalene sulfonate and 2-p-toluidinyl sulfonate.

It was found that interaction of the ionophore/cation complex with the fluorescent dyes produced enhanced fluorescence emission, increased lifetime and polarization, and significant blue-shift at the emission maxima of the fluorescence spectra. At constant concentrations of ionophore and fluorophore, the intensity of fluorescence emission was found to be a function of cation concentration.

2.4 Reporter Substances

As indicated supra, anionic dyes and fluorescers can be induced to enter the organic phase of a two-phase liquid system by the presence in that phase of a cation/ionophore complex. Thus these detectable anions can be said to "report" the presence of the cation trapped by the ionophore in the organic phase.

Other reporter substances which are not ionic in nature can be induced by the ionophore/cation complex to undergo a reaction yielding a detectable product. An example is the reaction sequence reported in U.S. Pat. No. 4,540,520 whereby a cation/ionophore complex induces a phenol to become deprotonated, thus initiating a coupling reaction to form a colored product. The so-called Gibbs Reaction is typical of such a reporter substance-producing reaction, in which 2,5-cyclohexadiene-1-one-2,6-dichloro-4-chloroimine couples with a deprotonated phenol to form a colored product and HCl.

2.5 Ionophores

The term "ionophore" embraces many diverse molecules, all of which are related by their unique capacity to bind with certain charged species to the relative exclusion of others, and which do so in a fashion which, at least to some degree, enables the ionophore molecule to electrically shield the ion from its environment. Indicative of this phenomenon is the liquid/liquid partitioning technique described above. The ionophore, because of its unique structure and its multitude of electron rich or electron deficient atoms ("donor atoms" or "receptor atoms", respectively) enables an ion such as sodium or potassium to enter a nonpolar organic phase.

Ionophores include naturally occurring compounds, such as valinomycin, as well as compounds of the structural categories of podands, corands, cryptands, hemispherands, spherands and cryptahemispherands.

2.5.1 Podands

Ions can be selectively complexed with certain acyclic compounds. For example, a linear chain which contains a regular sequence of electron rich donor atoms, such as oxygen, sulfur or nitrogen, has the capability of associating with positively charged ions to form complexes. The main structural difference between podands and other ionophores is the openness or acyclic nature of their structures. Thus, podands can be subcategorized into monopodands, dipodands, tripodands, etc. A monopodand, therefore, is a single organic chain containing donor or receptor atoms, a dipodand is two such chains connected to a central moiety capable of variable spacial orientation, and a tripodand is three chains attached to a central moiety.

2.5.2 Corands

The corands are monocyclic compounds which contain electron donor atoms or acceptor atoms, which are electron rich or deficient, and which are capable of complexing with particular cations or anions because of their unique structures. Included in this term are the crown ethers in which the monocyclic ring contains oxygen as the donor atoms. Other corands are compounds which contain an assortment of electron rich atoms such as oxygen, sulfur and nitrogen. Because of the unique sizes and geometrics of particular corands, they are adaptable to complexing with various ions. In so complexing, the electron rich atoms, such as the oxygens in a crown ether, become spacially oriented towards the electron deficient cation. The carbon atom segments of the chain are simultaneously projected in a direction outwards from the ion. Thus, the resultant complex is charged in the center but is relatively hydrophobic at its perimeter.

2.5.3 Cryptands

The cryptands are the polycyclic analogs of the corands. Accordingly, they include bicyclic and tricyclic multidentate compounds. In the cryptands, the cyclic arrangement of donor atoms is three dimensional in space, as opposed to the substantially planar configuration of the corand. A cryptand is capable of virtually enveloping the ion in three dimensional fashion and, hence, is capable of strong bonds to the ion in forming the complex. As with the corands, the donor atoms can include such atoms as oxygen, nitrogen and sulfur.

2.5.4 Hemispherands

Hemispherands are macrocyclic or macropolycyclic ionophore systems, such as cryptands, whose cavities are partially preorganized for binding by the rigidity of the hydrocarbon support structure and the spatial and orientational dictates of appended groups.

2.5.5 Spherands

Spherands are macrocyclic or macropolycyclic ionophore systems whose cavities are fully preorganized by their synthesis, as opposed to becoming organized during complexing such as with an ion.

2.5.6 Cryptahemispherands

Cryptahemispherands combine the partially preorganized cavity features of the hemispherand, but contain multiple other ligand-gathering features of the cryptands.

2.6 Chromogenic Ionophores

Certain compounds have been studied which are capable not only of behaving as ionophores by forming cation complexes but which, when so complexed, exhibit a detectable formation of or change in color. Thus, experiments were published in 1977 whereby chromophoric moieties were covalently attached to ionophores to achieve a color response to potassium (Tagaki, et al., *Analytical Letters*, 10 (13), pp. 1115–1122 (1977)). There it is taught to couple covalently a chromophoric moiety such as 4-pigryl-amino- to an ionophore such as benzo-15-crown-5. Moreover, U.S. Pat. No. 4,367,072 mentions many crown ethers, cryptands and podands covalently substituted with a chromophoric group, such as

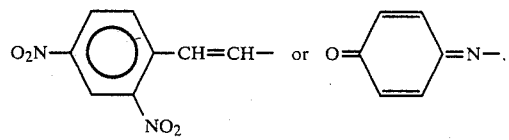

Yet another reference, German *Offenlegungschrift* 32 02 779, published Aug. 4, 1983 discloses a chromogenic cryptand structure.

2.7 Synopsis

Many technological developments have occurred since the early recognition that antibiotics such as valinomycin are capable of complexing certain ions and transporting them into the hydrophobic internal region of a cell membrane and, ultimately, into the cell nucleus. This basic ionophore discovery has led to the invention of a myriad of assay techniques for such ions as potassium, sodium, calcium and others; and has spawned a variety of diagnostic procedures of invaluable assistance to the chemist and physician. Moreover, countless new ionophore compounds have been discovered and invented of such chemical and structural diversity and complexity as to engender a whole new area of organic chemistry.

Certain applications of these technologies to ion determination, however, have met with problems. Although ionophores can possess high ion selectivity, the presence of high concentrations of other ions relative to the ion of interest can lead to interference in the desired result. Thus, if an ionophore were to have a specificity ratio of 50:1 for complexing with ion X+ over ion Y+, nevertheless if Y+ were present in solution at a concentration 50 times that of X+ the resultant selectivity of the system for X+ would be diminished to such a great extent as to render the ionophore practically useless as an assay reagent for X+. Such disparity of concentrations occurs, for example, in blood where normal sodium/potassium concentration ratios are in the neighborhood of 35:1.

Moreover, some prior art assays utilizing prior art ionophores have heretofore required a highly alkaline medium in order to function usefully, and aspects which contribute to poor shelf life as well as corrosiveness. Such systems also require a hydrophobic phase to contain or segregate the ionophore from the aqueous test sample, thus leading to organic/aqueous systems which respond relatively slowly.

Thus, it would be desirable to greatly increase selectivity in a chromogenic ionophore, thereby overcoming interference from competing ions present at much higher concentrations. Likewise, it would be desirable to obviate the need for harshly alkaline conditions and a multiphasic system. These and other unexpected advantages have been realized through utilizing the unique compounds described herein.

3. BRIEF DESCRIPTION OF THE DRAWINGS

The appended drawings are presented to further describe the invention, and to assist in its understanding through clarification of its various aspects.

FIGS. 1A, 1B and 1C describe a reaction pathway for synthesizing a preferred chromogenic cryptahemispherand discussed in Section 6.3 herein and shown in FIG. 5.

FIG. 2 portrays the linear dose/response curve obtained from the preferred embodiment of the invention described in Section 10.2 herein.

FIG. 3 shows the comparative data between the method of the present invention and the standard ISE method for potassium assay in random serum samples as described in Section 10.3 herein.

FIG. 4 provides a dose/response curve for various potassium levels utilizing the test device of the present invention described in Section 10.5 herein.

4. SUMMARY OF THE INVENTION

Figure 1A:
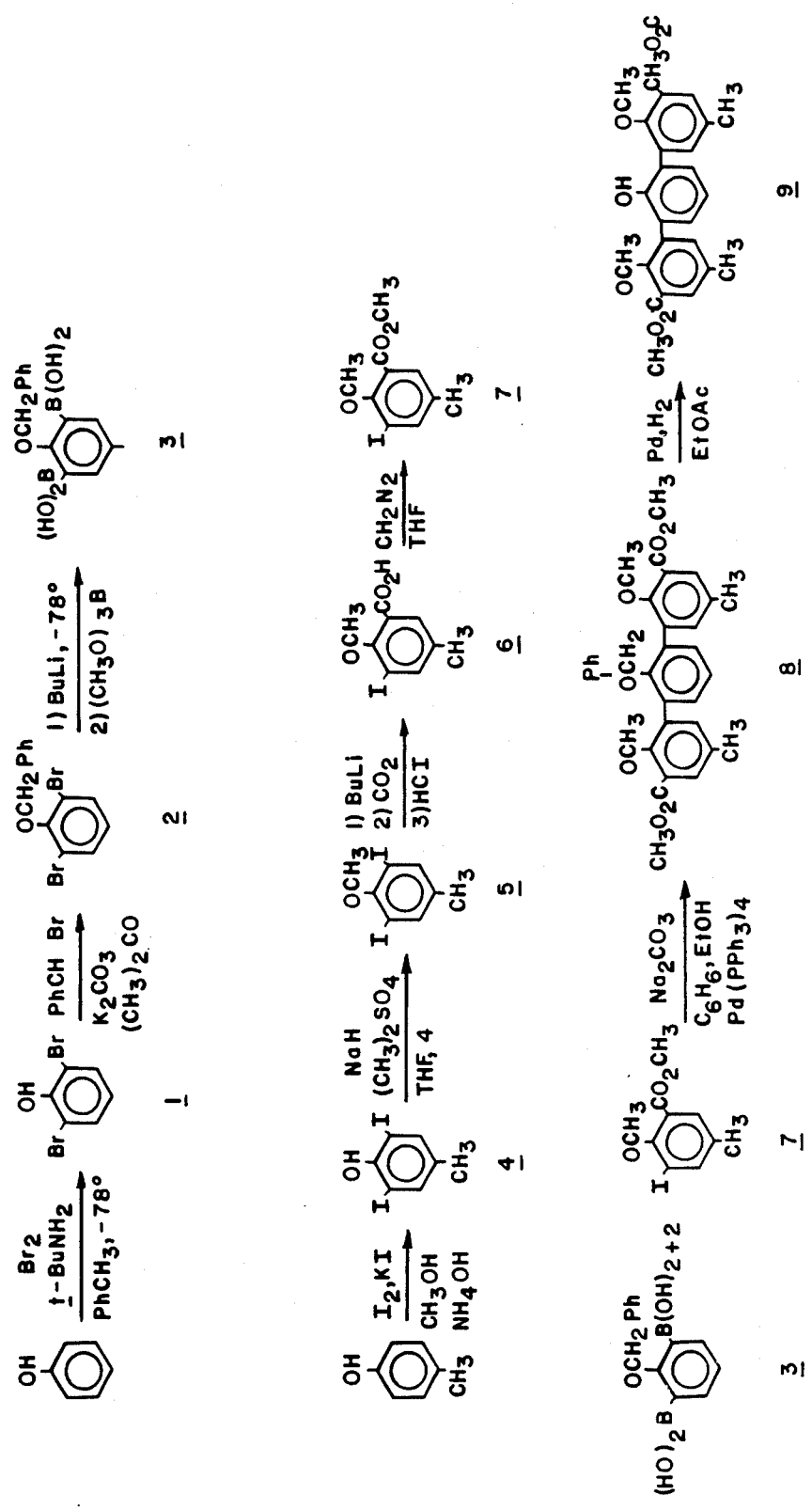

Briefly stated, the present invention resides in the discovery of a new class of compounds defined herein as "chromogenic cryptahemispherands", which have the structure (I):

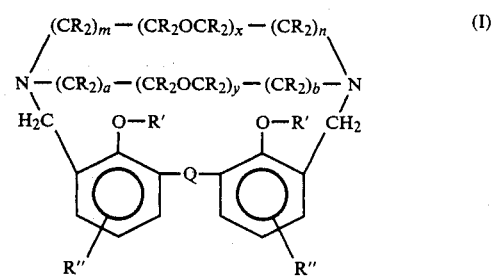

wherein:
R, same or different, is hydrogen, lower alkyl, lower alkylidene, lower alkenyl, allyl or aryl;

R', same or different, is lower alkyl, lower alkylidene, lower alkenyl, allyl or aryl;

R'', same or different, is hydrogen, lower alkyl, lower alkylidene, lower alkenyl, allyl or aryl;

Q is a chromogenic moiety capable of providing the appearance of or change in color, or which is otherwise capable of providing a detectable response in the presence of a particular cation;

a, b, m and n, same or different, are 1 to about 3; and x, y, same or different, are 1 to about 4.

This discovery led to further discoveries, including a composition for detecting the presence of an ion in solution, such as potassium and sodium, and a method for its use. The composition comprises the compound and a buffer capable of providing a pH in the range of about 5–9. Incorporation of the composition into a carrier matrix provides a dry test device for use in determining specific ions in solution. Both the composition and the device are utilized by contacting either with a test sample suspected of containing the ion of interest, and observing a detectable response.

Finally, the process for making the compounds of the present invention is a further part of the present invention, entailing truly innovative organic synthesis, and which enabled the synthesis of a preferred embodiment of the unique compounds of the present invention. The preferred process comprises a synthesis sequence such as is described in FIGS. 1A, 1B and 1C.

The scope of the invention, including the compound, composition and test device; and their use, synthesis and preparation, and experimental results are set forth in Sections 4–10 herein, and in the appended claims.

5. DEFINITIONS

Certain terms used in the present discussion should at this point be mentioned to assure that the reader is of the same mind as the authors as to their respective meanings. Thus the following definitions are provided to clarify the scope of the present invention, and to enable its formulation and use.

5.1 Ionophore

The term "ionophore" includes, broadly, molecules capable of forming a complex with an ion in solution. For example the cyclic polypeptide, valinomycin, binds selectively to potassium ions in solution to form a cationic complex. Also included in the term are crown ethers, cryptands, podands, spherands, hemispherands and cryptahemispherands.

5.2 Chromogenic

As used herein, "chromogenic" is intended as meaning that characteristic of a chemical system whereby a detectable response is generated in response to an external stimulus. Thus, for example, a cryptahemispherand is chromogenic where it is capable of exhibiting a detectable response upon complexing with an ion, which detectable response is not limited solely to change in color as defined below.

5.3 Detectable Response

By the term "detectable response" is meant a change in or appearance of a property in a system which is capable of being perceived, either by direct observation or instrumentally, and which is a function of the presence of a specific ion in an aqueous test sample. Some examples of detectable responses are the change in or appearance of color, fluorescence, phosphorescence, reflectance, chemiluminescence, or infrared spectrum which are referred to generally as chomogenic responses. Other examples of detectable responses may be the change in electrochemical properties, pH and nuclear magnetic resonance.

5.4 Lower Alkyl, Lower Alkylidene, Lower Alkenyl

The term "lower alkyl", as used in the present disclosure includes an alkyl moiety, substituted or unsubstituted, containing about 1-4 carbon atoms. Included in the meaning of lower alkyl are methyl, ethyl, n-propyl, isopropyl, n-butyl, sec-butyl and tert-butyl. These may be unsubstituted, or they may be substituted provided any such substituents do not interfere with the operation or functioning of the presently claimed test means or device in its capability to detect ions. "Lower alkylidene" is used in the same context as "lower alkyl", but designates an alkylene or alkylidine group (i.e., a divalent alkyl) having 1-4 carbon atoms. Thus, lower alkylidene includes methylene, ethylidene, n-propylidene, isopropylidene, n-butylidene, sec-butylidene and tert-butylidene. "Lower alkenyl" means vinyl or lower alkyl substituted vinyl.

Substituent groups can be selected with a wide degree of latitude, although in general they are chosen to accommodate the intended use of the ionophore of the present invention in complexing with a particular cation. Thus in the case where the cryptahemispherand is designed to complex with a cation such as potassium, the substituent is usually electrically neutral, such as hydrogen or methyl.

5.5 Aryl

By the term "aryl" is meant groups having one or more six-membered aromatic ring systems. Such ring systems can be heterocyclic, such as pyridinyl ($NC_5H_4-$), or can be homocyclic, such as phenyl ($C_6H_5-$), benzyl ($C_6H_5CH_2-$) and naphthyl. Aryl groups can be substituted or unsubstituted, provided that in the former case the substituent not interfere with the intended utility of the invention, i.e., the detection of ions in solution.

As in the case of substituent groups for lower alkyl and alkylidene, a wide latitude of substitution obtains for aryl groups, depending on the use of the ultimate chromogenic cryptahemispherand.

5.6 Electron Withdrawing Group

By the term "electron withdrawing group" is meant substituent groups such as $NO_2$, $CF_3$, CN, COOR.

6. THE CHROMOGENIC CRYPTAHEMISPHERAND

The chromogenic cryptahemispherand of the present invention, generically depicted as compound (I) in Section 4, supra, allows a significant degree of latitude as to its geometry and chemical nature, dependent upon selection of the variable parameters such as R, R', R'', Q, a, b, m and n, x and y. It is careful selection of these parameters that permits tailoring of the molecule to alter ion selectivity. Thus by following the teachings herein, molecules can be custom synthesized such that the internal cavity of the bicyclic structure can vary greatly as to its physical dimensions, and can be rendered more or less electron-rich.

As a result, very high selectivity for one ionic species in the presence of one or more other ions can be achieved. For example, the Experimental section, Section 10, infra, illustrates the measurement of potassium concentration in solutions which contain relatively high concentrations of sodium. Thus, it is not only the structure and chromogenicity of the present compound which render it unique, but also, and perhaps more importantly, its adaptability to being fashioned to suit the intended ion of interest, thereby achieving heretofore unattainable selectivity for one type of ion in solution in the presence of another, even when the concentration of the latter far outstrips the former.

Accordingly, each branch of the bicyclic system (I) is variable, both in physical dimension, degree of electron-richness or electron deficiency, and in the nature of substituent groups. For example, by varying the number of the groups $CR_2OCR_2$ in each of the chains in which it occurs, the electron density affecting the cavity can be designed to suit both the charge of the ion to be detected as well as its ionic radius and other physical dimensions.

6.1 Cationic Adaptability

The chromogenic cryptahemispherands of the present invention can be made adaptable to the detection of cations. The bridgehead nitrogen atoms are uncharged, and their unshared electron pairs are available to participate with other electron-rich atoms in the molecule in rendering it an electron-rich environment conducive to receiving and complexing with a cation. Moreover, because of the unique steric configurational aspects of the cavity of the molecule, contributed in part by the aromatic chain of the bicyclic structure, the molecule can virtually "lock in" the entrapped ion, thereby dramatically increasing the association constant, $K_a$, of the complex. Other ions in the test sample which might be attracted by the election-rich cavity are either too large to penetrate it or too small to be held by the cavity geometry and structure, thus leading in both cases to a very low $K_a$ for competing ions in comparison to that of the ion for which the bicyclic ionophore has been tailored.

6.2 The Chromogenic Moiety

Compound I includes as part of its structure a particular kind of chemically configured moiety, Q, which is capable of changing its physico-chemical characteristics when a complex is formed by an ion and compound (I). That is to say, if the target ion, i.e., the ion for which the structure of (I) has been tailored to selectively accept to form an ionophore/ion complex, is present in a test sample, whether or not other ions are present, a detectable change in those physico-chemical properties takes place. This capability of Q to exhibit such a response to complexation contributes greatly to the usefulness of (I) in assaying the analyte, or target, ion.

Whereas the concept of the chromogenic moiety Q is very broad, including within its scope a plethora of known and yet-to-be-discovered chemical and physical configurations, nevertheless several common threads exist among them, and are possessed by each. As the structure (I) indicates, Q must be divalent. Thus it is capable of bonding within the aromatic chain of the bicyclic structure through at least two covalent bonds. Secondly, as mentioned above, it must be capable of taking on different attributes when (I) is complexed with an ion than when (I) is in its uncomplexed state.

As presently contemplated, it is preferred that Q have the generic structure II:

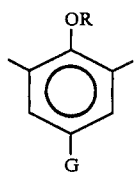
(II)

in which R is as defined supra and G is a chemical moiety which, when attached as depicted, acts by itself or in concert with the rest of the depicted structure (II) to form a detectable response to a complexed ion. Thus the concept of G is broad, and includes, but is not limited to, such chemical moieties as

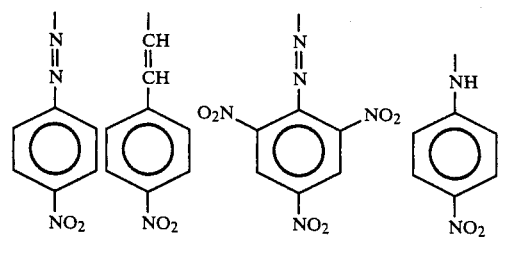

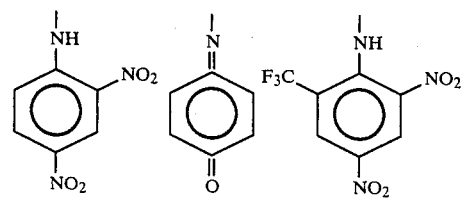

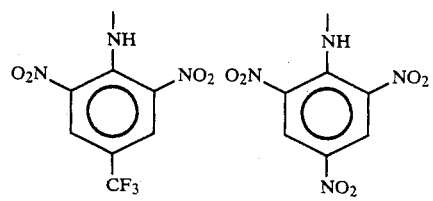

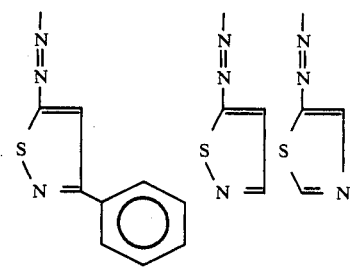

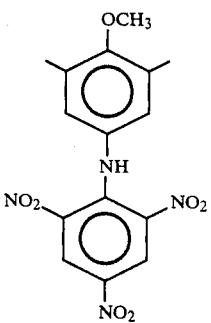

as well as any other moiety, known or to be discovered, which imparts to Q the desired detectability. Especially preferred for use as group G are 2,4,6-trinitroanilino; 2,6-dinitro-4-trifluoroethylanilino; 2,4-dinitro-6-trifluromethylanilino; 4-nitroanilino; 4-nitrophenylazo; 4-nitrostyryl; and 4-benzoquinonmonoimino. It has been found that compound (I) is especially useful when Q has the structure

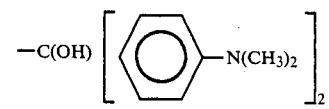
(III)

6.3 Presently Preferred Embodiment

Figure 5:
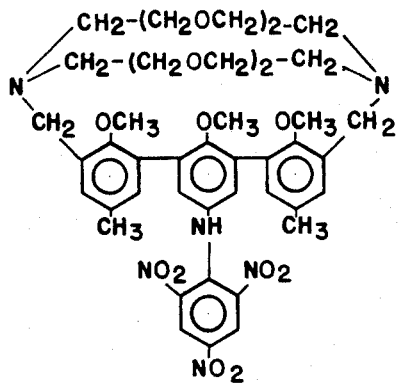
FIG. 5 depicts the structure of a preferred embodiment of the present invention whereby the compound shown is selective for potassium ion assay.

Of the myriad compounds embodied by the present disclosure, one which has been found especially selective in the determination of $K^+$, such as in blood, serum, and urine, is the compound having the structure of FIG. 5 derived from compound (I) wherein:

Q is compound (III);
R is hydrogen;
R' is $CH_3$;
R" is $CH_3$;
a and b are 1;
m and n are 1; and
x and y are 2.

The chromogenic cryptahemispherand of FIG. 5 has been found to exhibit unusually high selectivity for potassium ion, even in solutions having many times higher concentrations of other monovalent cations such as sodium. Moreover, compositions useful in such analyses can be formulated and used at a relatively mild pH, such as in the range of about 5-9, preferably between 6 and 8. Yet another advantage of the preferred embodiment is that it is capable of functioning in an essentially aqueous environment, without the attendant need of a separate hydrophobic phase. Thus, the latter disadvantageous requirements of prior art ionophoric test systems have been eliminated by the advent of the present invention.

7. THE TEST COMPOSITION

The discovery of the compounds previously described prompted further research which led to the formulation of a composition which, when prepared as an aqueous solution, was found useful for detecting the presence of certain ions, such as potassium, sodium, lithium, and others. Such composition includes, in addition to compound (I), the presence of a buffer to provide a pH environment of about 5 to about 9. Preferably the buffer provides a pH of about 6 to 8. In addition, the composition may contain manufacturing excipients, stabilizers, surfactants and other inert ingredients, all of which are easily within the ken of one skilled in the art, or which could be routinely determined at the bench without the need for undue experimentation.

In use the test sample is merely contacted with the composition and the detectable response is observed. In the case of the compound of FIG. 5, it has been found convenient to assess the response as light absorbed such as at 500 nanometers (nm). To a small amount of an aqueous test sample is added a relatively large volume of a solution of the compound of FIG. 5 at a pH of about 6-8. The mixture is put into a cuvette and observed spectrophometrically at about 500 nm. Experiments using varied known potassium concentrations yield a dose/response curve enabling clear correlation between change in absorbance corresponding to various potassium concentrations in the millimolar range.

8. THE TEST DEVICE

As the discovery of chromogenic compound (I) led to a composition useful for detecting certain ions, so the composition led to a test device, thereby still further extending the utility of the basic discovery comprising the overall invention. Thus, by incorporating a suitable carrier matrix with the composition, a test device is obtained which facilitates ion assay yet further.

Such a device lends itself to dry storage when not in use, thus enabling long shelf-life, and can be pressed into service immediately simply by contacting it with a small portion of the test sample, be it blood, serum, urine or other aqueous solution to be assayed. It can take on such formats as a dip-and-read strip for urine or a test slide for use with an automatic blood analyzer, or can from a multilayer structure such as is described in U.S. Pat. Nos. 3,992,158 and 4,292,272.

8.1 The Carrier Matrix

It is desirable that the carrier matrix comprise a porous or wettable material. Thus, in a single layer format the carrier matrix can be formed from materials such as paper, cardboard, porous polymers, polymer fiber and natural felts, and other suitable materials. Especially preferred as carrier matrix materials are filter paper, and porous high density polyethylene. In a multilayer analytical element format, the buffer can be stored in an upper layer and the chromogenic cryptahemispherand in a lower layer in a superposed laminar fashion. The matrices for these layers can be formed from materials such as gelatin, water soluble or water swellable polymers, and other suitable materials. In addition to these two layers, a spreading layer, a reflecting layer and a support material can be incorporated to form an integral analytical element.

8.2 Making the Test Device

The device is prepared by incorporating the carrier matrix with the test composition and, if desired, providing the dried matrix with a support.

Thus the composition is applied to the matrix by innoculating the surface of the matrix or by dipping it into a solution of the composition. The thus-impregnated matrix can then be dried at room temperature or at elevated temperatures, provided the temperature is not so high as to deleteriously affect the composition.

The dried, impregnated carrier matrix can then be mounted, if desired, on a suitable support such as a circumferential frame which leaves the matrix exposed in the middle; or the matrix can be mounted at one end of a plastic strip, the other end serving as a convenient handle.

Another way of making the test device, for the analysis of potassium for instance, can comprise the treatment of a porous high density polyethylene matrix with a surfactant to render it wettable, the impregnation of a reagent mixture containing the compound of FIG. 5, a binder and a buffer, and the drying of the reagent mixture on the porous matrix.

In use the test sample is contacted with the surface of the test device and the detectable response is measured at 580 nm or other wavelength on a reflectometer. Experiments using varied known potassium concentrations yield a dose/response curve enabling clear correlation between changes in percent reflectance and potassium concentration in the millimollar range.

9. USE OF THE INVENTION

The present invention can be adapted for use in carrying out a myriad of ion assays, both manually and on automated systems, which assays are applicable to a broad field. Not only is clinical chemistry part of that field, but also chemical research, chemical process control, and quality assurance are a few of the many possible applications of this technology. The composition and test device are well suited for use in clinical testing of body fluids such as blood, blood serum and urine, since in this work a large number of repetitive tests are frequently conducted, and test results are often needed soon after the test sample is taken from the patient.

The test composition and device are used by contacting with the test sample, and observing a detectable response. In a typical analytical procedure, a portion of test sample is placed on the test device for a sufficient period of time (such as several minutes). If desired, excess sample may be removed, such as by washing in a gentle stream of water with subsequent blotting with tissue paper, or washing in a gentle stream of water.

If the ion under analysis is present in the test sample, the complex of ionophore and ion will form, and a detectable response will appear. Where the moiety Q on compound (I) forms or changes color in response to the complex, such response is observed, either with the naked eye or instrumentally. Where Q is a fluorophore such as fluoroscein, a fluorescence spectrophotometer can be utilized to measure the detectable response formed in the test device (here, the appearance of or change in fluorescence). Other techniques useful in observing a detectable response include reflectance spectrophotometry, absorption spectrophotometry and light transmission measurements.

When the test sample is blood serum, transmission or reflectance techniques can be used to detect and quantify the presence of any reaction products, the formation of which serves as the detectable response. In this case radiant energy such as ultraviolet, visible or infrared radiation, is directed onto one surface of the test device and the output of that energy from the opposite surface is measured. Generally, electromagnetic radiation in the range of from about 200 to about 900 nm has been found useful for such measurements, although any radiation permeating the test means and which is capable of signifying the occurrence or extent of the response can be used.

Various calibration techniques are applicable as a control for the analysis. For example, a sample of analyte standard solution can be applied to a separate test means as a comparison or to permit the use of differential measurements in the analysis.

10. EXPERIMENTAL

A series of experiments was performed to investigate various aspects of the present invention. A description of experimental procedures and results is provided here to assist in the understanding of the basic concepts as well as to fully and clearly describe preferred embodiments.

10.1 Synthesis of a Preferred Chromogenic Cryptahemispherand

Figure 1B:
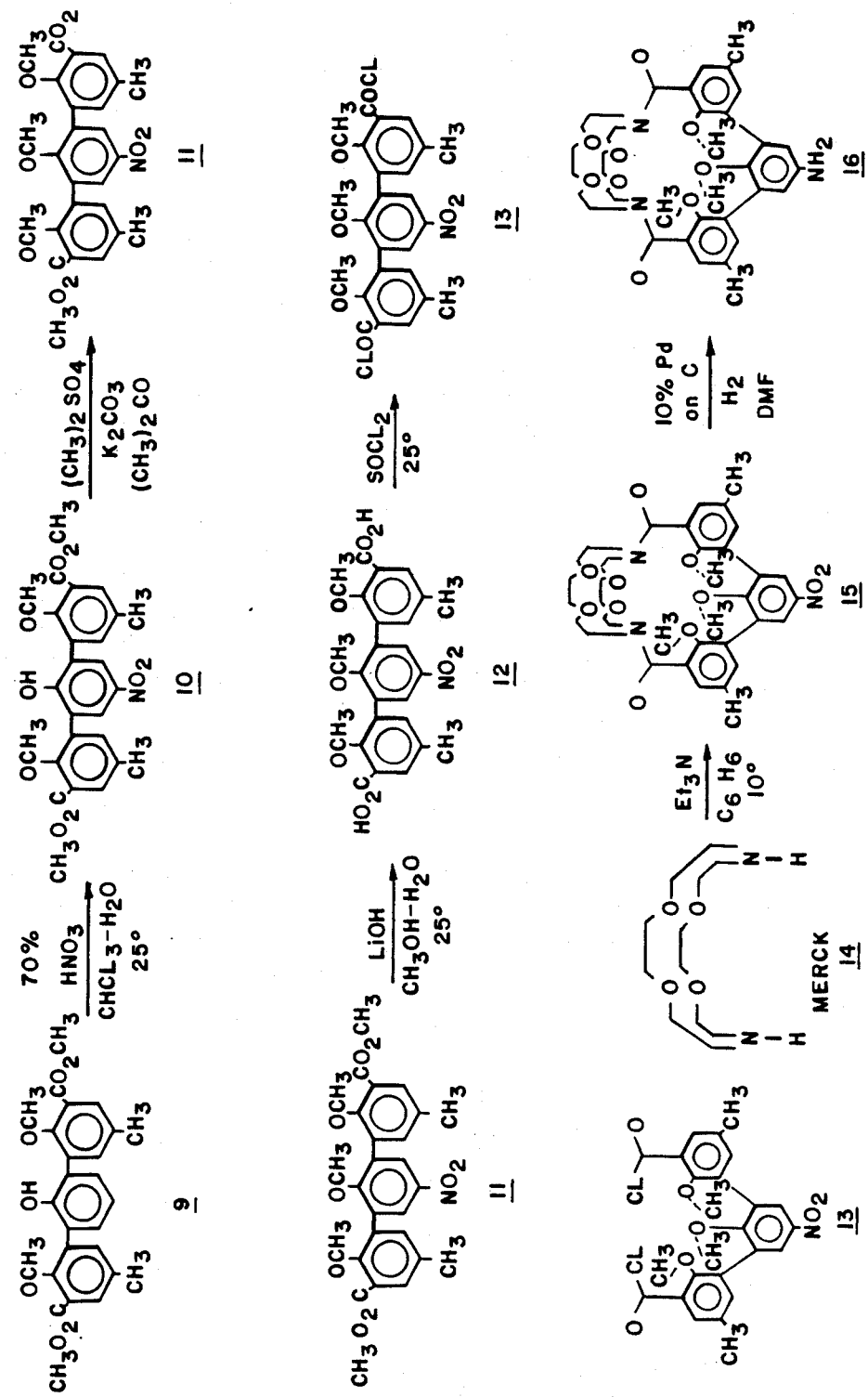

An experiment was performed to synthesize a preferred embodiment of compound (I), supra. The chromogenic cryptahemispherand prepared in this experiment is referred to in Section 6.3 as the compound of FIG. 5. The reaction pathway is depicted in FIGS. 1A, 1B and 1C.

Preparation of Compound 2

A suspension of 30 g (0.12 mol) of 1,[1] 34 g (0.2 mol) of benzyl bromide, and 30 g (0.22 mol) of anhydrous $K_2CO_3$ in 600 mL of acetone was refluxed for 48 hours (h), evaporated under reduced pressure, the residue was dissolved in $CHCl_3$ and $H_2O$ (600 mL of each) and the layers were separated. The organic extract was dried, concentrated to 50 mL, and added to an $Al_2O_3$ column (400 g) made up in 1:1 cyclohexane-benzene. Elution of the column with 3 L of 1:1 cyclohexane-benzene gave 32.6 g (80%) of 2 as a colorless oil. The $^1H$ NMR spectrum (200 MHz, $CDCl_3$) gave absorptions at δ5.04 (s, $OCH_2$, 2H) and 6.8–7.66 (m, ArH, 8H).
[1] Prepared in accordance with Pearson, D. E.; Wysong, R. D.; Breder, C. V. J. Org. Chem. 1967, 32, 2358–2360.

Preparation of Compound 3

To a solution of 13.3 g (38.9 mmol) of 2 in 350 mL of THF under Ar at −78° C. was added 85 mL of 1.3M sec-butyllithium (cyclohexane). After stirring 8 min, the lithiation solution was cannulated over 8 min into 150 g (1.4 mol) of trimethyl borate in 350 mL of THF at −78° C. The mixture was stirred 30 min at −78° C., warmed to 0° C. over 1 h, diluted with 500 mL of 2 N hydrochloric acid, and stirred 1 h at 25° C. Ether (0.8 L) was added, the mixture was stirred 8 h at 25° C., and the layers were separated. The aqueous layer was extracted with fresh ether (2×200 mL). Evaporation of the ether extracts (no drying) at 25°/30 mm gave 7.8 g (91%) of 3 as a moist oil which was stored at 5° C. and used without further purification. The 1H NMR spectrum [200 MHz, $(CD_3)_2CO$] absorptions at δ5.04 (s, $ArCH_2$, 2H) and 7.14–7.86 (m, ArH, 8H).

Preparation of Compound 5

To a solution of 120 g (0.33 mol) of 4 (iodination of commercially available p-cresol via literature preparation)[2] in 1 L THF at 0° C. under Ar was added 35 g (0.73 mol) of NaH (50% in mineral oil). After the vigorous reaction subsided, the cooling bath was removed, 76 g (0.6 mol) of dimethyl sulfate was added, and the mixture refluxed 6 h. The mixture was cooled to 25° C. and $CH_3OH$ was cautiously added to decompose excess dimethyl sulfate. Ethyl ether and 10% aqueous NaCl were added (600 mL of each), the layers were separated, and the organic layer was dried, evaporated and the residue was dissolved in 100 mL of cyclohexane. The solution was passed through a column containing 1 kg $Al_2O_3$ made up in petroleum ether. Elution of the column with $CH_2Cl_2$-petroleum ether mixtures (2–10% $CH_2Cl_2$) gave 5 as a colorless oil (lit. mp 25° C.)[3] in 82% yield (102 g). The $^1H$ NMR spectrum (200 MHz, $CDCl_3$) gave absorptions at δ2.24 (s, $ArCH_3$, 3H), 3.82 (s, $OCH_3$, 3H), and 7.57 (s, ArH, 2H).
[2] Burger, A., et al.; J. Am. Chem. Soc., 67, pp.1416–1419 (1945).
[3] Wilkinson, J. H., J. Chem. Soc., 626–627 (1951).

Preparation of Compound 6

A solution of 100 g (0.27 mol) of 5 in 1 L of ether under Ar was cooled to −78° C. A 110 mL portion of 2.5 M BuLi was added over 5 min and the resulting mixture stirred 10 min at −78° C. Carbon dioxide gas was vigorously bubbled through the suspension for 20 min, and the cold bath was allowed to warm to 25° C. over 10 h. The suspension was diluted with 600 mL of 1 N aqueous NaOH, and the layers were separated. The aqueous layer was acidified with 6 N HCl and the white solid collected and dried at 25° C. under vacuum to give 50 g (64%) of crude 6. The 1H NMR spectrum [200 MHz, $(CD_3)_2CO$] gave absorptions at δ2.33 (s, $ArCH_3$, 3H), 3.85 (s, $OCH_3$, 3H), 7.64 (d, ArH, 1H), and 7.86 (d, ArH, 1H).

Preparation of Compound 7

To a solution of 50 g (0.17 mol) of 6 in 400 mL of ether at 10° C. was added excess $CH_2N_2$ (in ether). After stirring 10 minutes at 25° C., the excess $CH_2N_2$ was decomposed with acetic acid and the ether evaporated. The residue was dissolved in 40 mL of $CH_2Cl_2$ and flash chromatographed on 300 g of silica gel made up in $CH_2Cl_2$. Elution of the column with $CH_2Cl_2$ gave 47 g (90%) of 7 as a colorless oil. The $^1H$ NMR spectrum (200 MHz, $CDCl_3$) gave absorptions at δ2.30 (s, $ArCH_3$, 3H), 3.85 (s, $OCH_3$, 3H), 3.92 (s, $OCH_3$, 3H), 7.59 (d, ArH, 1H), and 7.78 (d, ArH, 1H).

Preparation of Compound 8

To a mixture of 7.8 g (35 mmol) of 3 and 27 g (88 mmol) of 7 in 200 mL of benzene and 50 mL of ethanol under Ar was added 100 mL of 2M aqueous $Na_2CO_3$. To this vigorously stirred two-phase mixture was added 1.2 g (1 mmol) of tetrakis (triphenylphosphine)palladium and the mixture was refluxed 48 h (Note: 100 mg of fresh catalyst was added after 24 h reflux).[4] The layers were separated and the organic layer was dried, evaporated and dissolved in 40 mL of $CH_2Cl_2$. The mixture was separated by flash chromatography on silica gel (250 g) made up in $CH_2Cl_2$. Elution of the column with ether-$CH_2Cl_2$ mixtures (1 and 2% ether, 2 L of each) gave 12.8 g (67%) of 8 as a colorless foam. The $^1H$ NMR spectrum (200 MHz, $CDCl_3$) showed absorptions at δ2.32 (s, $ArCH_3$, 6H), 3.57 (s, $OCH_3$, 6H) 3.93 (s, $OCH_3$, 6H), 4.33 (s, $OCH_2$, 2H), and 6.60–7.61 (m, ArH, 12H).

[4] Modeled after Miyoura, N.; Yanagi, T.; Suzuki, A., *Syn. Comm.* 1981. 11(7), 513–519.

Preparation of Compound 9

A suspension of 2 g (2 mmol) of 10% palladium on carbon and 11.1 g (20.6 mmol) of 8 in 250 mL of ethyl acetate was hydrogenated (3 atm $H_2$) in a Parr shaker for 2 h. After filtration and evaporation of the ethyl acetate, the residue was dissolved in 30 mL of $CH_2Cl_2$ and purified by flash chromatograph on Si Gel (150 g) made up in $CH_2Cl_2$. Elution of the column with 2% ether-98% $CH_2Cl_2$ gave 7.1 g (77%) of 9 as a colorless foam. The $^1H$ NMR spectrum (200 MHz, $CDCl_3$) showed absorptions at δ2.38 (s, $ArCH_3$, 6H), 3.60 (s, $OCH_3$, 6H), 3.92 (s, $OCH_3$, 6H), and 6.97–7.63 (m, ArH, 7H).

Preparation of Compound 10

To a stirred solution of 7.1 g (15.8 mmol) of 9 in 500 mL of 1:1 $CHCl_3$—$CH_3CO_2H$ was added 20 mL of 70% $HNO_3$ over 2 min. After stirring 15 min, the solution was diluted with $H_2O$ (1.2 L) and $CHCl_3$ (200 mL) and the organic layer was extracted with $H_2O$ (3×1.2 L), dried, concentrated to 25 mL and flash chromatographed on Si Gel (200 g) made up in $CH_2Cl_2$. Elution of the column with $CH_2Cl_2$ (1 L) and 49:1 $CH_2Cl_2$-$ET_2O$ (3 L) gave 7.1 g (91%) of 10 as a yellow foam. The $^1H$ NMR spectrum (200 MHz, $CDCl_3$) gave absorptions at 2.42 (s, $ArCH_3$, 6H), 3.65 (s, $OCH_3$, 6H), 3.94 (s, $OCH_3$, 6H), 7.36 (d, ArH, 2H), 7.72 (d, ArH, 2H), and 8.30 (s, ArH, 2H).

Preparation of Compound 11

A mixture of 7.1 g (14.3 mmol) of 20, 20 g (0.16 mol) of dimethyl sulfate and 22 g (0.16 mol) of $K_2CO_3$ in 500 mL of acetone under Ar was refluxed 24 h, evaporated and the residue dissolved in 1 L of 1:1 $CHCl_3$-$H_2O$. The organic layer was dried, concentrated to 25 mL and flash chromatographed on 200 g of Si Gel made up in $CH_2Cl_2$. Elution of the column with $CH_2Cl_2$ (1 L) and 49:1 $CH_2Cl2$-ether (2 L) gave 6.8 g (93%) of 11 as a colorless foam. The $^1H$ NMR spectrum (200 MHz, $CDCl_3$) gave absorptions at δ2.39 (s, $ArCH_3$, 6H), 3.30 (s, $OCH_3$, 3H), 3.60 (s, $OCH_3$, 6H), 3.94 (s, $OCH_3$, 6H), 7.34 (d, ArH, 2H), 7.68 (d, ArH, 2H), and 8.25 (s, ArH, 2H).

Preparation of Compound 12

To a solution of 8 g (15.7 mmol) of 11 in 325 mL of CH OH was added 100 mL of $H_2O$ and then 12 g (0.29 mol) of LiOH·$H_2O$. After stirring 14 h at 25° C., the mixture was dilute with 400 mL of $H_2O$, extracted with $CH_2Cl_2$ (2×50 mL) and the aqueous layer acidified to pH 1 with concentrated HCl. Extraction of the aqueous suspension with ether (3×300 mL) and drying for 16 h at 95°/0.01 mm gave 5.6 g (74%) of 12 as an amorphous yellow powder. The $^1H$ NMR spectrum [200 MHz, $(CD_3)_2CO$] gave absorptions at δ2.42 (s, $ArCH_3$, 6H), 3.37 (s, $3OCH_3$, 3H), 3.65 (s, $OCH_3$, 6H), 7.45 (d, ArH, 2H), 7.75 (d, ArH, 2H), and 8.25 (s, ArH, 2H).

Preparation of Compound 13

A suspension of 2.44 g (5 mmol) of 12 in 8 mL (110 mmol) of purified thionyl chloride was stirred 2 h at 25° C. under Ar (12 dissolved after ∼30 min). Dry benzene (30 mL) was added and the solution evaporated at 40° C./30 mm to remove the excess thionyl chloride. This procedure was repeated three times. The crude product was dried at 25° C./0.01 mm to give 2.6 g (∼100%) of 13 as a yellow foam and was used without further purification. The $^1H$ NMR spectrum (200 MHz, $CDCl_3$) gave absorptions at δ2.44 (s, $ArCH_3$, 6H), 3.33 (s, $OCH_3$, 3H), 3.66 (s, $OCH_3$, 6H), 7.44 (d, ArH, 2H), 8.00 (d, ArH, 2H), and 8.32 (s, ArH, 2H).

Preparation of Compound 15

Compound 13 (2.6 g, 5 mmol) was dissolved in 150 mL of anhydrous benzene and transferred in 50 mL portions to a 50 mL gas-tight syringe. Similarly, 1.3 g (5 mmol) of 14 (available from Merck Chemicals) together with 1.5 g (15 mmol) of triethylamine was dissolved in 150 mL of anhydrous benzene and transferred to a 50 mL gas-tight syringe. These solutions were added via a syringe pump to an oven-dried 2 liter Morton flask containing 1200 mL of anhydrous benzene over 2 h with vigorous mechanical stirring under Ar at 12° C. After stirring for 8 h at 12° C., the suspension was warmed to 25°, filtered to remove triethylamine hydrochloride and evaporated. The residue was dissolved in 40 mL of $CH_2Cl_2$. Elution of a silica gel column with acetone-dichloromethane mixtures (10–30% of acetone) gave 2.1 g (60%) of 15 as a white solid which darkens above 320° C. and melts/decomposes at ∼345° C. The mass spectrum (70 eV) showed a molecular ion at m/e 707. The $^1H$ NMR spectrum (200 MHz, $CDCl_3$) showed absorptions at δ2 37 (s, $ArCH_3$, 6H), 2.85 (s, $OCH_3$, 3H), 3.41 (s, $OCH_3$, 6H), 3.05–3.88 (m, $NCH_2$, $OCH_2$, 22H), 4.30 (d, $NCH_2$, 2H), 7.17–7.23 (m, ArH, 4H), and 8.35 (s, ArH, 2H).

Preparation of Compound 16

A suspension of 560 mg (0.79 mmol) of 25 and 1 g of 10% palladium on charcoal in 200 mL of dimethylformamide was hydrogenated (3 atm $H_2$) in a Parr shaker for 2 h. The catalyst was removed by filtration and the filtrate diluted with $CHCl_3$ (500 mL) and $H_2O$ (1.2 L) and the layers were separated. The organic layer was extracted with fresh $H_2O$ (3×1.2 L), dried ($K_2CO_3$) and evaporated to give 520 mg (97%) of 16 as a colorless foam. The $^1H$ NMR spectrum (200 MHz, $CDCl_3$) showed absorptions at δ2.32 (s, $ArCH_3$, 6H), 2.66 (s, $OCH_3$, 3H), 3.41 (s, $OCH_3$, 6H), 3.06–3.96 (m, $NCH_2$, $OCH_2$, 22H), 4.28 (d, $NCH_2$, 2H), 6.80 (s, ArH, 2H), 7.08 (s, ArH, 2H), and 7.13 (s, ArH, 2H).

Preparation of Compound 17

A solution of 490 mg (0.72 mmol) of 16 in 100 mL of THF was heated to reflux under Ar and 2.0 mL (20 mmol) of borane-methyl sulfide was added. The methyl sulfide-THF was slowly distilled from the mixture over 70 min. The remaining solution (30 mL) was cooled to 5° C., 5 N aqueous NaCl was cautiously added to decompose excess borane, and THF (30 mL) and 5 N aqueous NaCl (50 mL) were added. The mixture was stirred for 10 days at 25° C., the THF was evaporated and the residue was extracted with $CH_2Cl_2$ (2×50 mL). The organic extracts were filtered through phase separator paper, concentrated to 5 mL and diluted with 150 mL of CH$_3$OH. After adding 0.4 g (4.8 mmol) of NaHCO$_3$ and 0.2 g (0.81 mmol) of picryl chloride to the CH$_3$OH solution and stirring 25 min. at 25° C., the mixture was diluted with CH$_2$Cl$_2$ (40 mL) and 100 mL of 1 N aqueous NaCl. The layers were separated, and the organic layer (no drying) was added to a silica gel column (100 g) made up in 2% CH$_3$OH-98% CH$_2$Cl$_2$. Elution of the column with CH$_3$OH—CH$_2$Cl$_2$ mixtures (2–5% CH$_3$OH) gave 40 mg (6%) of the 17 KCl complex. The NMR spectrum (200 MHz, CDCl$_3$) showed absorptions at $\delta 2.36$ (s, ArCH$_3$,6H), 2.84 (s, OCH$_3$, 3H), 3.48 (s, OCH$_3$ 6H), 2.18–4.10 (m, NCH$_2$, 24H), 2.67 (d, ArCH$_2$N, 2H), 4.20 (d, ArCH$_2$N,2H), 7.03 (d, ArH, 2H), 7.12 (d, ArH, 2H), 7.17 (s, ArH, 2H) and 9.09 (s, ArH, 2H).

Further elution of the column with CH$_3$OH-CH$_2$Cl$_2$ mixtures (10–20% CH$_3$OH) gave 250 mg (38%) of 17 NaCl complex as an orange foam. A Fab mass spectrum (m-nitrobenzyl alcohol dispersion) gave a base peak at m/e 883 (M+23) corresponding to the M+Na ion and a lower intensity ion at 899(M+39, 25% intensity of 883) corresponding to the M+K ion. The $^1$H NMR spectrum of 17·NaCl (200 MHz, CD$_2$Cl$_2$) showed absorptions at $\delta 2.33$ (s, ArCH$_3$, 6H), 2.12–4.00 (m, NCH$_2$, OCH$_2$, 24H), 2.95 (d, ArCH$_2$N, 2H), 4.06 (d, ArCH$_2$N, 2H), 4.06 (d, ArCH$_2$N, 2H), 7.0–7.13 (m, ArH, 6H) and 8.85 (s, ArH, 2H).

10.2 A Preferred Aqueous System for Potassium Determination

An experiment was conducted to assess the performance of the present invention in the analysis of potassium ion in an aqueous system, in a presently preferred embodiment.

Accordingly, a reagent solution of the invention was prepared by dissolving 15 mg of the compound of FIG. 5, as its sodium salt, in 1.65 mL diethylene glycol monoethyl ether. To this was added 48 mL of 0.1M HEPES buffer[5] (pH=7.3), followed by 0.17 mL of Brij-35[6] solution (30% w/v) in distilled water, and the mixture thoroughly stirred.

[5] HEPES buffer is prepared by adding 2.38 g of N-2-hydroxyethylpiperazine-N-2-ethane sulfonic acid to 90 mL distilled water, adding sufficient 1M tetramethylammonium hydroxide to bring the pH to 7.3, and adding distilled water to bring the volume to 100 mL. [6] Brij-35 is polyethoxylauryl ether A spectrophotometric automated instrument known as the RA-1000®system available from Technicon Instruments Corporation was used to assay the samples. The following instrument parameters were used:
Sample volume: 5.5 μl
Reagent volume: 385.0 μl
Optical filter: 500 nm
Temperature: 37° C.
Delay: 5 min.
Assay Type: end point
Calibration Factor: 1.0

Figure 2:
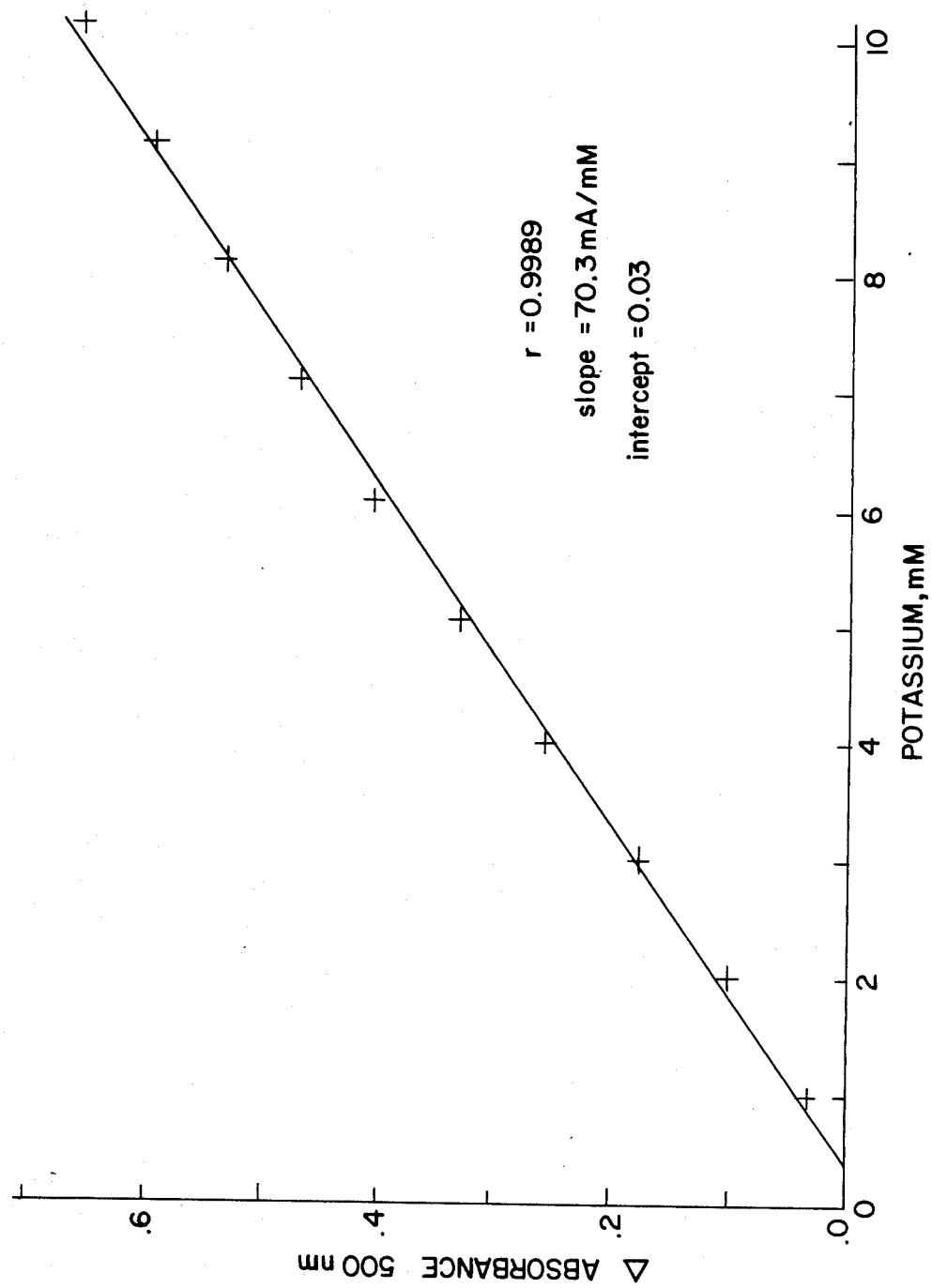

The spectrophotometric data obtained from this procedure is shown in FIG. 2, wherein potassium concentration is plotted against the change in light absorbance ($\Delta$Absorbance) at 500 nm. It can be seen that a linear dose-response curve, having a slope conducive to easy differentiation between absorbence levels, is obtained.

Results

The preferred aqueous system of the present invention yielded a linear dose/response curve with a slope enabling easy point differentiation using photometric methods ($\Delta$absorption at 500 nm).

10.3 Use of Preferred Aqueous System for Potassium Determination in Serum

An experiment was conducted to compare the present invention with an art-established procedure for measuring potassium in serum.

A series of random serum samples containing a broad range of potassium concentration was obtained. These were analyzed on a RA-1000 ® system as in 10.2, supra, and also by the RA-1000 ® ISE mode. The instrument parameters were the same as those in Section 10.2 for the light absorbance mode.

Results

Figure 3:
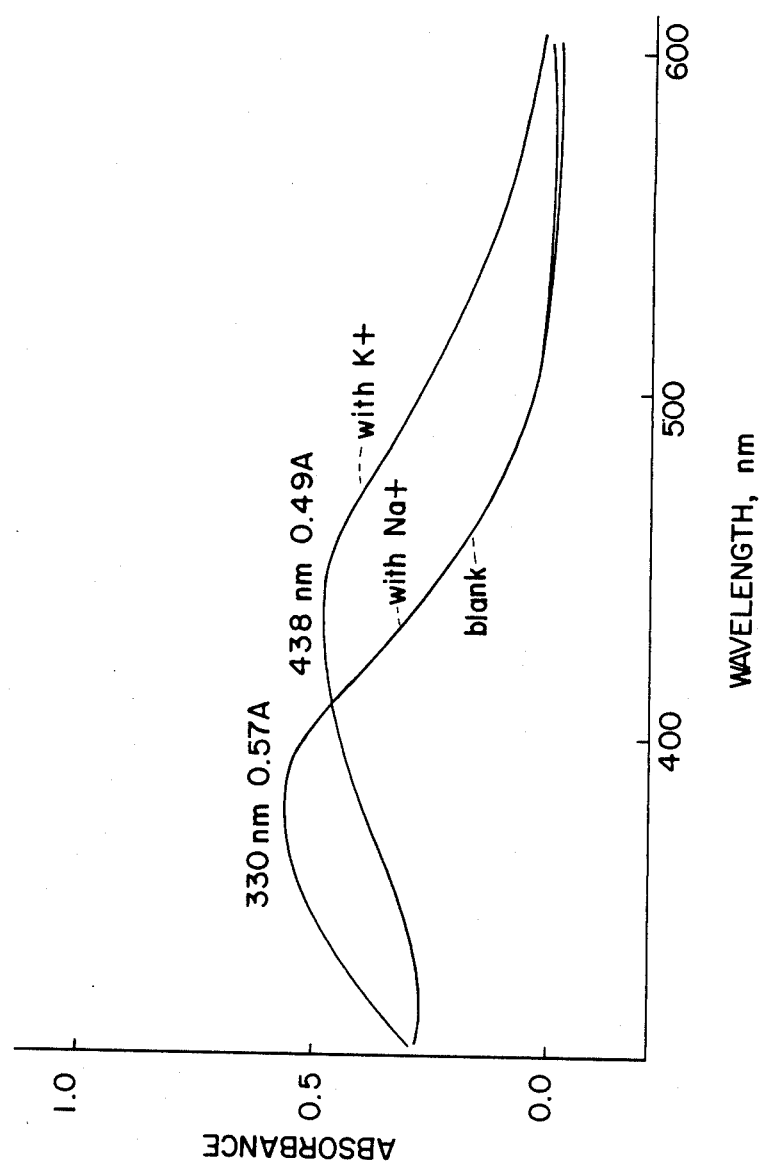

The comparative data is shown in FIG. 3, and shows excellent correlation between the method of the present invention and the standard ISE method for potassium concentrations in the range of 1–10 mM.

10.4 Effect of pH on Potassium/Sodium Selectivity in a Liquid/Liquid Partitioning System An experiment was conducted to study the selectivity of a compound of the present invention for potassium ion in the presence of sodium ion, where the pH of the aqueous phase was varied within an extraction system containing an immiscible organic solvent.

Two sets of 6 test samples were prepared, one containing potassium chloride, the other sodium chloride. Stock buffer solutions were prepared at pH 5.0, 6.0, 7.0, 8.0, 9.0 and 10.0. To a 2.0 ml aliquot of each solution was added 0.1 mL of 0.1 M KCl to form the first set of samples. The procedure was repeated except 0.1 mL of 0.1 M NaCl was used instead of KCl to form the second set of samples. To each sample was then added 2 mL of $7\times10^{-5}$M of the compound of FIG. 5 in methylene chloride. Each sample was then thoroughly agitated on a Vortex mixer for 1–2, minutes. The samples were set aside briefly to allow phase separation, and the absorbance of the CH$_2$Cl$_2$ phase was then measured at 300–700 nm on a Beckman DU-8 spectrophotometer. A blank sample was run to provide a control. The blank was prepared as indicated above except that deionized water was used instead of KCl or NaCl solution.

Results

The results are shown in Table 1 in terms of change in light absorbance from the control data at 450 nm ($\Delta$A). The data shows that significant response to both sodium and potassium occurred at pH levels in the range of 7.0 to 10.0, indicating poor discrimination between K$^+$ and Na$^+$, whereas at pH levels below 7.0, selectivity ratios of from 17.1 to 5.4 were obtained. This increase in ion selectivity with lowering pH was unexpected.

TABLE 1

| Effect of pH on Sodium and Potassium Response Utilizing Extraction in CH$_2$Cl$_2$ ($\Delta$ A at 450 nm) | | | | | | |
|---|---|---|---|---|---|---|
| | pH | | | | | |
| | 5.0 | 6.0 | 7.0 | 8.0 | 9.0 | 10.0 |
| Na$^+$ | 0.009 | 0.054 | 0.509 | 0.475 | 0.493 | 0.400 |
| K$^+$ | 0.154 | 0.293 | 0.682 | 0.503 | 0.586 | 0.493 |

10.5 Effect of pH and a Water-Miscible Organic Solvent on Potassium/Sodium Selectivity in an Aqueous System An experiment was conducted to show the effects of (a) pH and (b) the concentration of a water-soluble organic solvent, on a preferred aqueous system of the present invention. Accordingly, solutions of KCl and NaCl were prepared in water at varying pH levels using standard buffers and with varying amounts of dioxane added.

Aqueous 0.1M buffer solutions were prepared, to yield solutions at a pH of 6;0, 6.6, 7.0, 8.0, and 9.0. To each of these was added an amount of the compound of FIG. 5 in dioxane to assure a final concentration of 0.1 mM of the compound of FIG. 5. The volume of dioxane was varied to achieve concentrations of 1%, 25% and 50% by volume of dioxane. Thus three sets of reagent solutions were prepared, all being 0.1 mM of the compound of FIG. 5. Each set comprised the 5 pH levels, but each set varied from one another in dioxane percentage.

To 2.0 mL of each sample of reagent was added 0.1 mL of 1.0 M NaCl or KCl in water in an optical cuvette. Following mixing, light absorbance was measured on a Beckman DU-8 spectrophotometer at 300–700 nm. The data is shown in Table 2.

TABLE 2

Effect of pH and Dioxane on Sodium and Potassium Responses ($\Delta$ A at 450 nm) to the Compound of FIG. 5 in Aqueous Medium

| Dioxane | | 6.0 | 6.6 | 7.0 | 8.0 | 9.0 |
|---|---|---|---|---|---|---|
| 1% | $Na^+$ | 0.005 | 0.000 | 0.002 | 0.026 | 0.000 |
|  | $K^+$ | 0.003 | 0.414 | 0.512 | 0.098 | 0.006 |
| 25% | $Na^+$ | 0.002 | 0.001 | 0.000 | 0.016 | 0.086 |
|  | $K^+$ | 0.014 | 0.035 | 0.018 | 0.352 | 0.175 |
| 50% | $Na^+$ | 0.002 | 0.000 | 0.013 | 0.039 | 0.072 |
|  | $K^+$ | 0.032 | 0.012 | 0.007 | 0.061 | 0.005 |

Results

In one set of data, that utilizing pH 7 solutions (0.1M HEPES buffer) with 1% dioxane, no response to sodium was detected, whereas a considerable response to potassium occurred. Accordingly, the present invention exhibits an enormously high selectivity ratio for potassium over sodium at neutral pH with negligible organic solvent present (See FIG. 3). Such unexpected selectivity in chromogenic ionophores is heretofore unreported.

The overall data in Table 2 shows that as the organic solvent portion of the reagent was increased, both selectivity and sensitivity for potassium over sodium decreased. This phenomenon is contrary to results described in previously published works, where other ionophores, particularly crown ethers and cryptands, exhibited increased sensitivity and selectivity with increasing porportions of organic reagents. The present invention exhibits the reverse phenomenon.

Moreover, sensitivity and specificity appears inversely proportional to pH, whereas the above-mentioned previous results with other ionophores generally exhibited the opposite tendency.

10.6 A Model Test Device

An experiment was performed to prepare a test device of the present invention capable of detecting the presence of potassium, whereby a carrier matrix of high density polyethylene (HDPE) was incorporated with the compound of FIG. 5.

Porous disks having ½ inch diameters, a thickness of 1/32 inch, and a 35 um pore size were obtained from Porex Technologies, Inc., Fairburn, GA. These were pretreated by saturating with a 1% w/v solution of Surfynol 104 nonionic detergent (Air Products, Inc.) in chloroform and drying. The disks were then each treated with 30 uL of reagent solution. The stock reagent solution comprised a mixture of 0.9 mL distilled water, 0.1 mL diethylenglycolmonoethyl ether, 5 mg of the compound of FIG. 5 and 40 mg polyvinylpyrrolidone. The treatment comprised depositing on one side of each disk a 30 uL aliquot of stock reagent solution, which permeated the entire disk, and allowing the disks to dry at room temperature for five hours with subsequent storage in a dessicator charged with anhydrous calcium sulfate for 2 hours.

The disks were tested by innoculation with 25 uL of analytical specimens of 0.2 M MES buffer[7] at pH 6, containing concentrations of 1.0 mM, 2.0 mM, 3.0 mM, 5.0 mM and 7.5 mM, respectively, in potassium.

[7] 2-(N-morpholino) ethane sulfonic acid

Following 2 minutes incubation with analytical specimen, the disks were observed at 580 nm for reflectance data using an Infra-Alyzer ® (Technicon Instruments Corporation) modified for use in the visible portion of the electromagnetic spectrum.

Results

Reflectance measurements R were transformed into K/S values utilizing the well-known equation of Kubelka and Munk $$K/S = \frac{(1 - R)^2}{2R}$$

Figure 4:
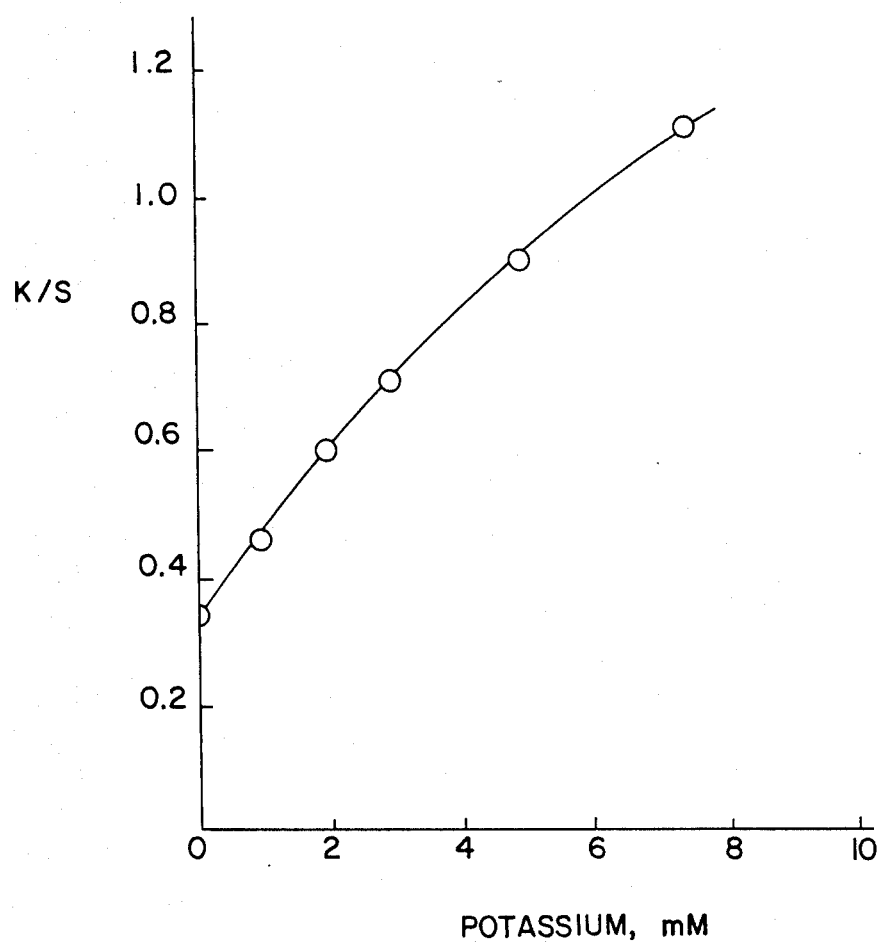

K/S values are plotted against potassium concentration in FIG. 4. The curve demonstrates that the test device possesses ideal sensitivity for potassium in the clinical range.

10.7 Test Device for Detecting Potassium in Serum

A porous high density polyethylene substrate, 35 um pore size and 1/32 inch thick was die cut into ½ inch diameter disks. These disks were rendered hydrophic by treatment with 1% Surfynol 104 (Air Products and Chemicals, Wayne Pennsylvania) in chloroform and drying. A thirty microliter reagent aliquot containing 0.4M imidazole-phosphoric acid buffer at pH 5.8, 6% polyvinylpyrrolidone (MW 40,000), 0.02% Brij-35 (ICI Americas Inc., Wilmington, Del.), 10% 2-ethoxyethoxy ethanol, and 9 millimolar compound of FIG. 5 was deposited to each porous high density polyethylene disk. These reagent impregnated disks were allowed to dry at ambient conditions for four hours before being used for potassium measurement.

To test the response of these dry test devices to various concentrations of potassium ions in serum samples, thirty microliters serum test sample was applied to each disk and incubated at room temperature for five minutes. The color changes were recorded on a reflectometer at 580 nm. The change in percent reflectance (%R) is indicative of a colorimetric response. The result is summarized in Table 3.

To evaluate the accuracy of the determination of potassium ion in human serum samples, the same samples obtained from a hospital were analyzed for potassium using a flame photometer and compared with the potassium values obtained using the dry test device method. Correlation data between the two methods are as follows: slope, 0.995; intercept, 0.063; correlation coefficient, r, 0.991.

TABLE 3

Response of the compound of FIG. 5 to potassium ions in serum on "dry" test devices.

| [K$^+$] mM | Response (% R) |
|---|---|
| 2 | 26.5 |
| 4 | 21.7 |
| 6 | 18.6 |
| 8 | 17.5 |
| 10 | 16.5 |

10.8 A Preferred Aqueous System for Sodium (Rate) Measurement

An experiment was conducted to assess the performance of one example of the present invention in the analysis of sodium ion in an essentially aqueous reaction system.

Figure 6:
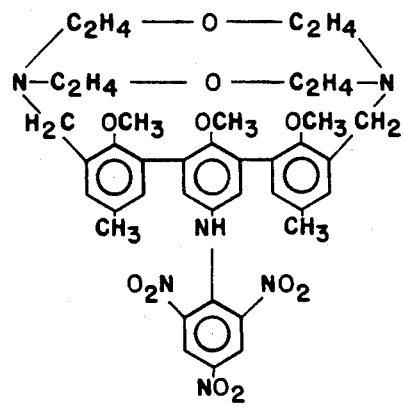
FIG. 6 depicts the structure of a preferred embodiment of the present invention whereby the compound shown is selective for sodium ion in a rate measurement.

Accordingly, a reagent solution was prepared by dissolving 18 mg of the compound of FIG. 6 as its lithium bromide complex, in 1.65 mL diethyleneglycol monoethyl ether. To this was added 48 ml of 0.2M HEPES buffer pH 7.3 followed by 0.13 mL of TRITON X-100 and the mixture thoroughly stirred.

The RA-1000® from Technicon Instruments was used to assay samples by discerning the change in absorbance of individual sample and reagent mixtures over a period of nine minutes and using the following instrument parameters:

Sample volume: 4.0 μl
Reagent volume: 395 μl
Optical filter: 500 nm
Temperature: 37° C.
Delay: 15 sec.
Incubation: 9 min.
Calibration Factor: 1.0
Printer Format: 3
Assay Type: rate The spectrophotometric data obtained from this procedure with aqueous sodium chloride calibrants is linear over the clinically significant range of 80mM to 200mM sodium in human serum. Specific values for the calibration curve are: slope, 0.0023 Δabsorbance units per mM in sodium concentration, intercept −3.025; correlation coefficient, r, 0.9996.

To evaluate the accuracy of the determination of sodium ion in human serum, samples obtained from a hospital were analyzed for sodium using the RA-1000® Ion Selective Electrode and compared with the sodium values obtained using the spectrophometric method. Correlation data between the two methods are as follows: slope, 1.059; intercept, −8.82; correlation coefficient, r, 0.9852.

10.9 A Preferred Aqueous System for Sodium (End Point) Measurement

Figure 7:
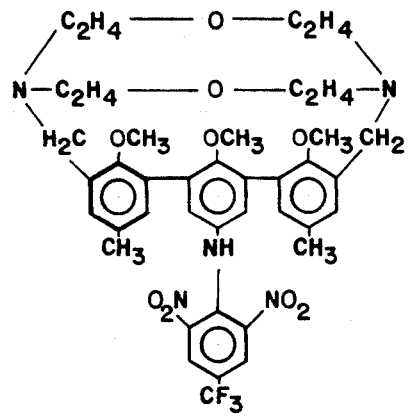
FIG. 7 depicts the structure of a preferred embodiment of the present invention whereby the compound shown is selective for sodium ion in an end point determination.

The performance of another example of the present invention was assessed for the assay of sodium in serum samples using an essentially aqueous reaction system. Accordingly, 33 mg of the compound of FIG. 7 as its lithium bromide complex, were dissolved in 1.65 mL of diethyleneglycol monoethyl ether. To this was added 48 ml of 0.2M HEPES buffer pH 8.1 followed by 0.085 mL of Brij .35 30% (w/v) and the mixture thoroughly stirred.

The RA-1000® from Technicon Instruments was used to assay samples by discerning the change in absorbance of the reaction mixture after sample is added. The following parameters were used on the instrument:

Sample volume: 2 μL
Reagent volume: 400μL
Optical filter: 550 nm
Temperature: 37° C.
Delay: 9 mins.
Calibration factor: 1.0
Printed format: 3
Assay Type: end point The spectrophotometric data obtained from this procedure showed a linear relationship between the change in absorbance of the reaction mixture and the logarithm of the sodium ion concentration in the sample over the clinically significant range of 80 mM to 200 mM, with a sensitivity of about 0.002 absorbance unit per mM change in sodium concentration.

Comparison of serum samples assayed by this spectrophotometric method and by the RA-1000® Selective Electrode method were also made. Correlation data between the two methods are as follows: slope, 0.963; intercept, 6.22; correlation coefficient, r, 0.9946.

10.10 Test Device for Detecting Sodium Ions

A porous high density polyethylene substrate, 35 un pore size and 1/32 inch thick was die cut into ½ inch diameter disks. These disks were rendered hydrophilic by treatment with 1% W/V surfynol 104 (Air Products and Chemicals, Wayne, Pa.) in chloroform and drying. A thirty microliters reagent aliquot containing 0.2M imidazole-phosphoric acid buffer pH 7.5, 0.2% W/V Triton X-100 (Rohn and Haas Co., Philadelphia, Pa.), 10% W/V 2-ethoxyethoxyethanol, 7% W/V polyvinylpyrrolidone (MW 40,000), and 3 millimolar compound of FIG. 6 was deposited to each porous high density polyethylene disk. These reagent impregnated disks were allowed to dry at ambient conditions for four hours before being used for sodium measurement.

To test the response of these dry test devices to various concentrations of sodium ions in aqueous medium, thirty microliters aqueous test solution was applied to each disk and incubated at 37° C. for six minutes. The color changes were recorded on a reflectometer at 560 nm. The change in percent reflectance (%R) is indicative of a colorimetric response. The result is summarized in Table 4. The data clearly show that the compound of FIG. 6 can be used to detect sodium ions in a dry test device.

TABLE 4

Response of the compound of FIG. 6 to sodium ions in aqueous medium on dry test devices.

| [Na$^+$] mM | Response (% R) | K/S |
|---|---|---|
| 0 | 21.4 | 1.443 |
| 2 | 18.2 | 1.838 |
| 4 | 17.6 | 1.929 |
| 6 | 16.9 | 2.043 |
| 8 | 16.5 | 2.113 |
| 10 | 15.2 | 2.365 |
| 15 | 14.0 | 2.641 |

What is claimed is:

1. A method for selectively determining the presence of a test cation in a test sample, comprising the steps of:
   (a) contacting said test sample with a compound which complexes selectively to the test cation and being of the formula:

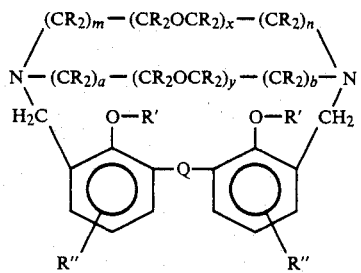

wherein:
R, the same or different, is hydrogen, lower alkyl, lower alkylidene, lower alkenyl, allyl or aryl;
R', the same or different, is lower alkyl, lower alkylidene, lower alkenyl, allyl or aryl;
R", the same or different, is hydrogen, lower alkyl, lower alkylidene, lower alkenyl, allyl or unsubstituted aryl;
Q is a chromogenic moiety capable of providing a detectable response upon the complexation of said compound with said test cation;
a, b, m and n, the same or different, are 1 to 3;
x is 1 to 4; and
y is 1 to 4; and
y is 1 to 4; and
(b) measuring said detectable response.

2. The method of claim 1 wherein said chromogenic moiety Q of said compound has the structure:

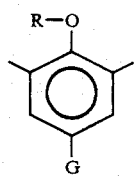

wherein G is 2,4,6e-trinitroanilino; 2,6-dinitro-4-trifluoromethylanilino; 2,4-dinitro-6-trifluoromethylanilino; 4-nitro-anilino; 2,4-dinitrophenylazo; 4-nitrophenylazo; 4-nitrostyryl; and 4-benzoquinonmonoimino.

3. The method of claim 2 wherein when R is not hydrogen, said chromogenic moiety Q has the structure:

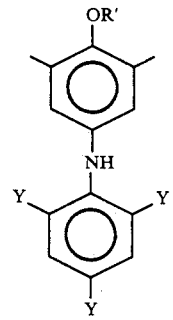

wherein:
Y, the same or different, is an electron withdrawing group such as CN, $NO_2$, $CF_3$ or COOR wherein R is hydrogen, lower alkyl, lower alkylidene, lower alkenyl, allyl or aryl.

4. The method of claim 3, wherein G is 2,4,6-trinitroanilino, 2,6-dinitro-4-trifluoromethylanilino, 2,4-dinitro-6-trifluoromethylanilino or 4-nitroanilino.

5. The method of claims 1 to 4 wherein said compound is incorporated into a solid carrier member with a buffer capable of providing a pH in the range of about 5-9, and contacting said test sample with said solid carrier member.

6. A test device for determining the presence of a test cation in an aqueous test sample pursuant to the method of one of claims 1-4, said device comprising a solid carrier member, the compound of one of claims 1-4 incorporated into said solid carrier member and a buffer incorporated into said carrier member capable of providing a pH in the range of about 5-9.

* * * * *